United States Patent [19]

Ferree et al.

[11] Patent Number: 4,670,029
[45] Date of Patent: Jun. 2, 1987

[54] WATER TREATMENT SYSTEM FOR ULTRASONIC INSPECTION OF TURBINE ROTORS FROM THE BORE

[75] Inventors: Herbert E. Ferree; Lawrence D. Nottingham, both of Hempfield Township, Westmoreland County, Pa.

[73] Assignee: Westinghouse Electric Corp., Pittsburgh, Pa.

[21] Appl. No.: 862,332

[22] Filed: May 12, 1986

[51] Int. Cl.⁴ ............................................. B01D 19/00
[52] U.S. Cl. ...................................... 55/189; 55/195; 73/61.1 R; 141/48
[58] Field of Search ........................... 55/55, 189, 195; 73/61.1 R; 141/48

[56] References Cited

U.S. PATENT DOCUMENTS 3,255,575  6/1966  Roberts ............................. 55/195 X
4,492,639  1/1985  Stewart et al. ............. 73/61.1 R X Primary Examiner—Charles Hart
Attorney, Agent, or Firm—F. J. Baehr, Jr.

[57] ABSTRACT

A system for deaerating water utilized to flood a bore of a turbine rotor which is to be ultrasonically inspected in which the bore is inclined and evacuated and heated water enters the bore and impinges on a surface that breaks up the influent stream of water to substantially increase its surface area to assist in the deaeration, the bore being connected to a trough partially filled with heated water to a level above the bore to maintain the flooded condition of the bore during the ultrasonic inspection.

18 Claims, 2 Drawing Figures

WATER TREATMENT SYSTEM FOR ULTRASONIC INSPECTION OF TURBINE ROTORS FROM THE BORE

BACKGROUND OF THE INVENTION

This invention relates to a water treatment system and more particularly to a water treatment system for ultrasonically inspecting turbine rotors from flooded bores.

Utilizing a flooded bore allows the transducers in an ultrasonic inspection system to be removed some distance from the bore surface so that the sonic indications near the surface can be distinguished as the area adjacent the bore is highly stressed and the condition of this portion of a rotor is important in determining life expectancy of the rotor.

One of the problems associated with such an ultrasonic inspection is the formation of air bubbles on the bore surface which diffuses and attenuates the ultrasonic signals. Deaerating the water removes dissolved gases to assist in eliminating the air bubbles on the bore surface.

SUMMARY OF THE INVENTION

In general, a system for deaerating liquid utilized to flood a bore of a shaft which is to be ultrasonically inspected comprises a first sealing means placed on one end of the shaft for capping the bore, a second sealing means at the other end of the shaft for capping the bore, a vacuum pump in fluid communication with the bore through the first sealing means to evacuate the bore and means for admitting liquid into the evacuated bore in such a manner that the liquid is deaerated as it enters the evacuated bore, thus filling the bore with liquid having a minimal amount of air bubbles at the bore surface.

BRIEF DESCRIPTION OF THE DRAWINGS

The objects and advantages of this invention will become more apparent by reading the following detailed description in conjunction with the accompanying drawings, in which.

DESCRIPTION OF THE PREFERRED EMBODIMENT

Figure 1:
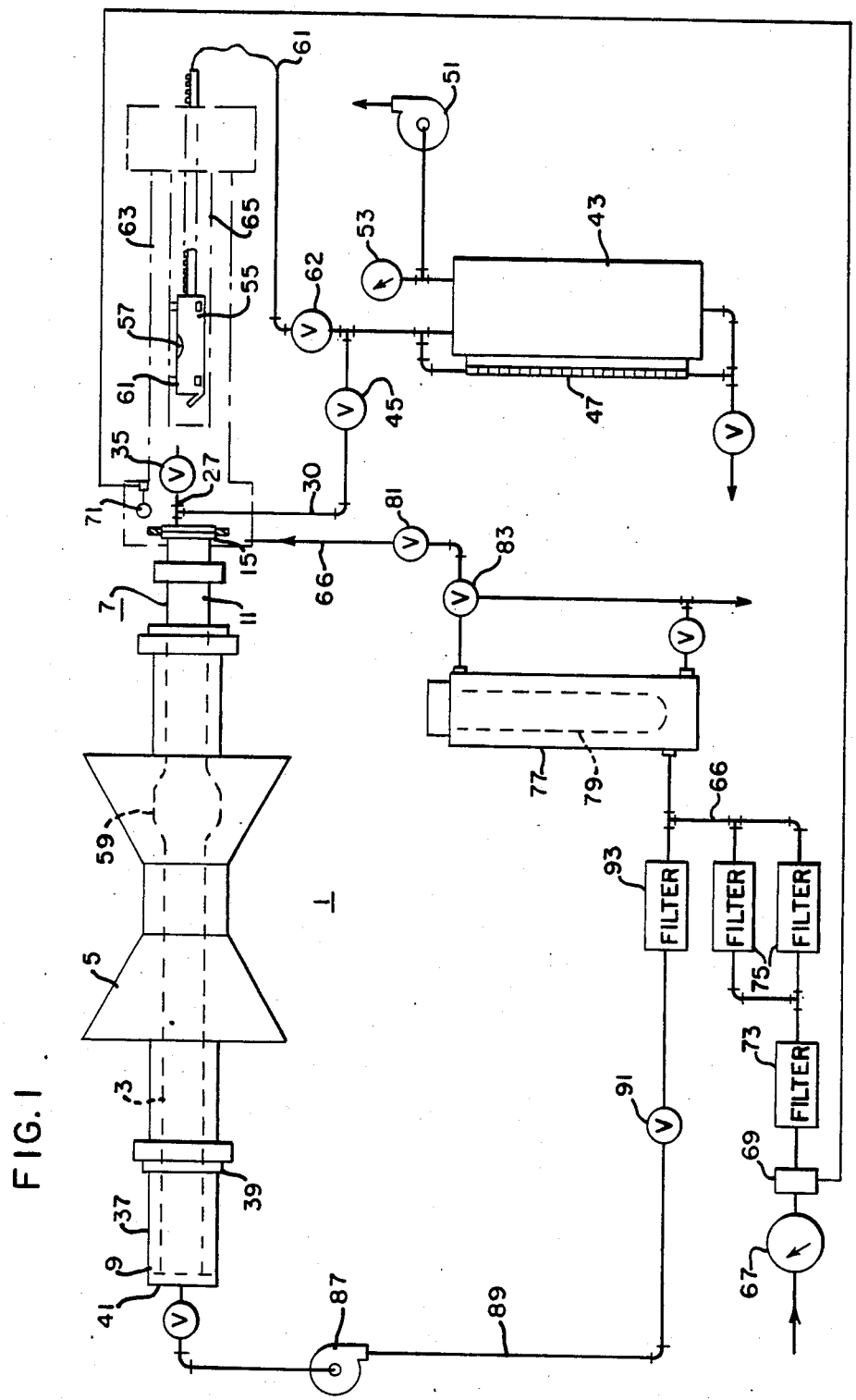
FIG. 1 is a schematic drawing of a water treatment utilized for ultrasonically inspecting a turbine rotor from the bore.

Referring now to the drawings in detail and in particular to FIG. 1, there is shown a system 1 for deaerating water or other liquid utilized to fill a bore 3 of a turbine rotor 5 that is to be ultrasonically inspected from the bore.

The system 1 comprises a first cap 7 or other sealing means for sealing one end of the bore 3 and a second cap 9 or other sealing means on the other end of the bore. The bore must be sealed to withstand a vacuum generally in the range of less than one inch of mercury absolute or less than 0.5 psia.

Figure 2:
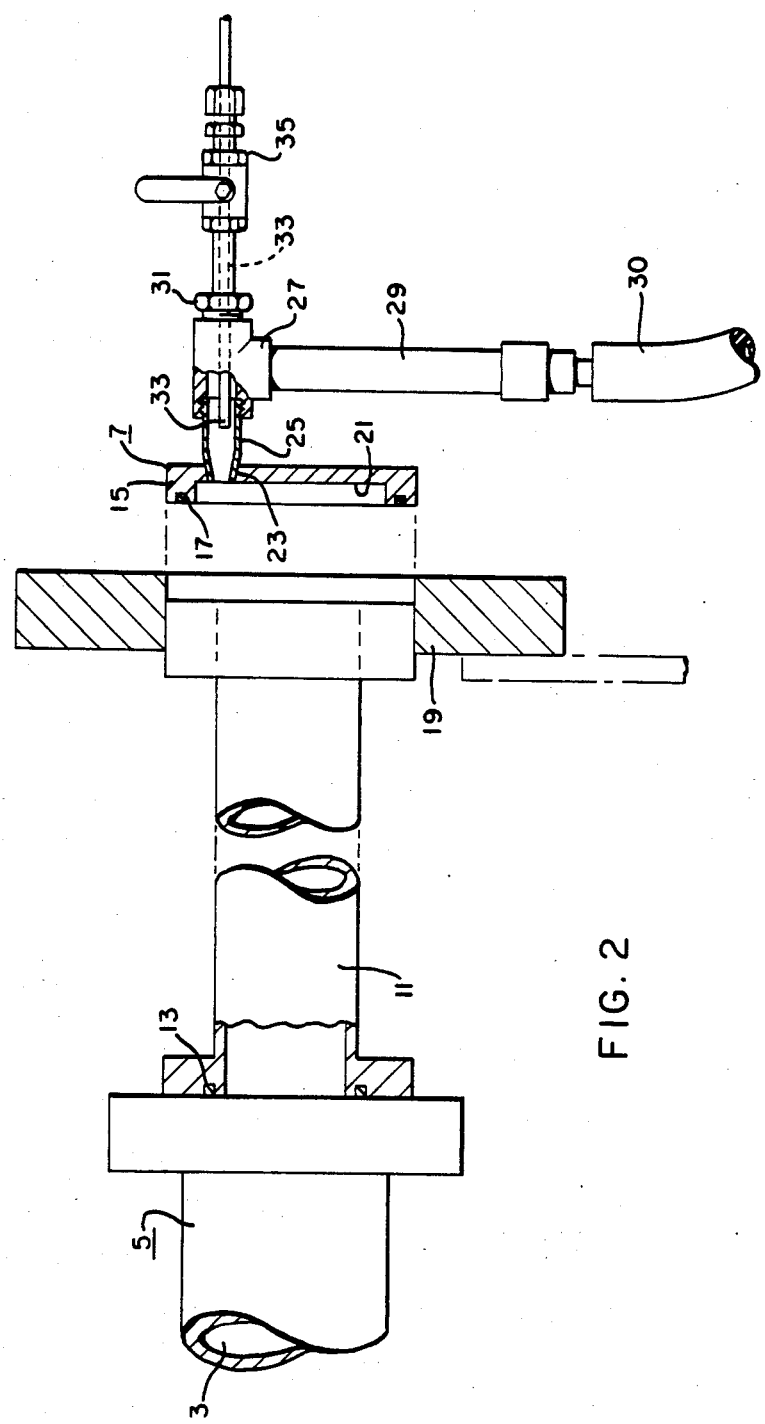
FIG. 2 is an enlarged view of a seal flange and piping utilized to evacuate the bore and deaerate the influent water utilized to fill the bore.

The first cap 7, as shown in FIG. 2, comprises a spool piece 11 which is sealed to the bore by an O-ring 13 or other sealing means and blind flange 15 which also utilizes an O-ring 17 or other sealing means to form a seal between the blind flange 15 and the spool piece 11. A flange-like tube support 19 is disposed on the end of the spool piece and cooperates with the blind flange 15 to form a seal. The blind flange 15 has a recess 21 forming a generally round indentation in the blind flange 15. The indentation is larger in diameter than the opening in the spool piece 11. In the outer portion of the recess 21 is a threaded hole 23 which receives a short nipple 25. Screwed onto the nipple 25 is a tee 27 and a short piece of pipe 29. The pipe 29 forms the stem of the tee and is connected to a vacuum line 30. Also connected to the tee 27 is a coupling 31 which has a small diameter tube 33 extending therethrough. The small diameter tube 33 extends through the tee 27 and into the short nipple 25. A valve 35 is connected to the small diameter tube 33.

The second cap 9 as shown in FIG. 1 comprises a tubular portion 37 made of a transparent material and has a flange 39 which is sealed adjacent the bore 3 and an end plate 41 closing the other end of the tubular portion 37.

The vacuum line 30 is connected to a tank or vessel 43 having a large volume and a valve 45 is disposed in the line 30 between the tank 43 and the tee 27. The tank 43 has a site glass 47 to determine the amount of water collected therein and a drain valve 49 to drain the water from the tank.

A vacuum pump 51 is also connected to the tank 43 along with a vacuum gauge 53.

An ultrasonic head 55 for inspecting the rotor 5 is also shown schematically in FIG. 1 and comprises at least one dynamically focused transducer 57 disposed thereon. The ultrasonic head 55 is inserted into a flooded bore when the blind flange 15 is removed. To remove trapped air and air bubbles from a flooded bore having a bottle bore portion as indicated at 59, a tube 61 extends from the ultrasonic head 55 to the bore surface and is connected to the tank 43 via tubing 61, which has a valve 62 disposed adjacent the tank 43.

Also shown schematically in FIG. 1 is a trough 63 having a tubular support 65 for the ultrasonic head 55. The tubular support 65 and trough 63 are aligned with the bore 5 which is inclined upwardly toward the trough 63. The trough 63 is partially filled with water and maintained at a level above the bore of the spool piece 7. Water is supplied to the trough through a line 66 which has disposed therein a meter 67, a solenoid valve 69 controlled by a float 71 in the trough 63 maintains a constant water level in the trough 63. A particle filter 73 and a pair of charcoal filters 75 filter the influent water. The water then flows through a heater 77 having a calrod or other heating means 79 disposed therein. After passing through the heater 77, a needle valve 81 controls the rate of flow into the trough 63. A safety or pressure relief valve 83 bypasses the water to a drain and generally operates if the pressure in the heater exceeds 75 psi.

A recirculating pump 87 is disposed in a line 89 connecting the second cap 9 and to the heater 77 and has a check and control valve 91 and particle filter 93 disposed therein.

The deaerating system is housed in an enclosure described in detail in a copending application entitled, "Apparatus For Ultrasonically Inspecting a Liquid-filled Bore in a Large Shaft," filed Mar. 26, 1986 and assigned Ser. No. 844,499, which application is hereby incorporated by reference.

The operation of the apparatus is as follows:

The rotor shaft 5 is inclined upwardly toward the trough 63 and the trough 63 with the transparent tube 65 and spool piece 11 is aligned with the inclined bore 3. The ends of the bore 3 are sealed with caps 7 and 9.

The vacuum pump 51 is turned on, evacuating the tank 43 and the valve 45 is opened to evacuate the bore 3 to a pressure in the range of 0.5 psia. Water heated to about 115° F. by the heater 77 is fed into the trough 63 via the line 66, filling the trough 63 to a predetermined level above the support tube 65 as set by the float switch 71. After the vacuum in the bore reaches somewhere in the neighborhood of 0.5 psia, the valve 35 is opened, allowing the water from the trough 63 to enter the bore 3. As the influent water flows through the tube 33, it impinges on the flange 19, breaking up the influent stream to substantially increase the surface area of the influent water and enhance the deaeration. During the process of filling the bore, if the water level in the tank 43 builds up to some predetermined level indicated in the site glass 47, the valve 45 is closed along with the valve 35, sealing off the bore. The vacuum pump 51 is stopped and water is drained from the tank 43 by opening the drain valve 49. The drain valve is closed when the water level is no longer visible in the site glass and the pump 51 is turned on to evacuate the tank 43 to a pressure in the range of O.5 psia. Once this pressure is attained, the valve 45 is opened and the evacuation of the bore continues. When the pressure level in the bore is in the order of 0.5 psia, the water inlet valve 35 is again opened to continue filling the bore 3. This process is repeated until the bore 3 is filled.

Once the bore 3 is filled, valve 45 is closed, the vacuum is vented, the blind flange 15 is removed and a calibration block (not shown) is placed in the trough and the ultrasonic head and transducer are moved to adjacent the calibration block to begin the ultrasonic inspection procedure. To assist in removing air bubbles which may collect in the bore 5, particularly in a counterbored area, as indicated at 59, the vacuum tube 61 which extends radially outwardly from the ultrasonic head is connected to the tank 43 and the valve 62 is opened to remove any bubbles of air that are entrapped in the bottle-bore portion 59.

To inhibit rust within the bore and within the deaerating apparatus, a rust inhibitor, such as Immunol 1809 supplied by the Harry Miller Corporation, is added to the water. The meter 67 may be utilized to determine the amount of water in the system from which it can be determined the amount of rust inhibitor that should be added.

Utilizing the bore 3 as a deaerating chamber not only deaerates the water but also removes air from the bore 3 prior to filling it with the deaerated water. Tilting the bore 3 minimizes the amount of air trapped in bottle-bore portions 59 and assists in removing air bubbles which have a tendency to accumulate adjacent the top of the bore.

What is claimed is:

1. A system for deaerating liquid utilized to flood a bore of a shaft which is to be ultrasonically inspected, comprising:
    a first sealing means placed on one end of said shaft for capping said bore;
    a second sealing means at the other end of said shift for capping said bore;
    a vacuum pump in fluid communication with said bore said first sealing means to evacuate said bore, and means for adding liquid into said evacuated bore in such a manner that the liquid is deaerated as it enters said evacuated bore to fill said bore with liquid having a minimal amount of air bubbles within the bore.

2. A system for deaerating liquid as set forth in claim 1 and further comprising means for heating the liquid before it enters the bore.

3. A system for deaerating liquid as set forth in claim 1, wherein the means for admitting liquid into the bore in such a manner that the liquid is deaerated, comprises a surface upon which influent liquid impinges as it enters the evacuated area.

4. A system for deaerating liquid as set forth in claim 1, wherein the first sealing means is disposed in a trough having a liquid level which is maintained above the first sealing means.

5. A system for deaerating liquid as set forth in claim 4 and further comprising means for heating the liquid in the trough to assist in deaeration.

6. A system for deaerating liquid as set forth in claim 5, wherein the means for heating the liquid in the trough is external to the trough.

7. A system for deaerating liquid as set forth in claim 1 and further comprising means for separating liquid from the air being evacuated from the bore, wherein the separating means is disposed between the bore and the vacuum pump.

8. A system for deaerating liquid as set forth in claim 7, wherein the means for separating the liquid from an air being evacuated from the bore comprises an enclosed vessel with a large volume so that the velocity of the air and liquid passing therethrough is low, allowing separation of the liquid from the air being evacuated.

9. A system for deaerating liquid as set forth in claim 8, wherein the enclosed vessel has means for determining the level of liquid therein, and means for draining the liquid therefrom.

10. A system for deaerating liquid as set forth in claim 1 and further comprising a tube which is disposed in an ultrasonic head and is in fluid communication with the vacuum pump to remove air bubbles trapped in an enlarged portion of the bore.

11. A system for deaerating liquid as set forth in claim 9 and further comprising a recirculation pump in fluid communication with the bore through the second sealing means and serially in fluid communication with heating means and a trough whereby fluid is circulated from the bore through the heating means and into the trough where it can reenter the bore when the first bore sealing means is opened to the trough.

12. A system for deaerating liquid as set forth in claim 11 and further comprising a filter interposed between the circulating pump and the heater.

13. A system for deaerating liquid as set forth in claim 12 and further comprising a fill line in fluid communication with the heater and connected to a supply of liquid.

14. A system for deaerating liquid as set forth in claim 13 and further comprising a liquid flowmeter disposed in the fill line.

15. A system for deaerating liquid as set forth in claim 14 and further comprising a valve operable by the liquid level in the trough to maintain a predetermined liquid level in the trough.

16. A system for deaerating liquid as set forth in claim 15 and further comprising filter means disposed between the liquid supply and the heater.

17. A system for deaerating liquid as set forth in claim 16, wherein the first sealing means comprises an enclosed tubular extension into which an ultrasonic head can be extended.

18. A system for deaearting liquid as set forth in claim 17 and further comprising a valve disposed between the second sealing means and the recirculating pump.

* * * * *